United States Patent [19]
Farber

[11] Patent Number: 5,549,914
[45] Date of Patent: Aug. 27, 1996

[54] HEAT STABLE WOUND CARE GEL

[75] Inventor: Elliott Farber, North Mankato, Minn.

[73] Assignee: Sween Corporation, N. Mankato, Minn.

[21] Appl. No.: 316,401

[22] Filed: Sep. 30, 1994

Related U.S. Application Data

[63] Continuation-in-part of Ser. No. 145,039, Oct. 29, 1993, abandoned, which is a continuation of Ser. No. 992,264, Dec. 14, 1992, abandoned.

[51] Int. Cl.$^6$ .............. A61K 9/10; A61K 47/32; A61K 47/42; A61K 47/36
[52] U.S. Cl. .............. 424/487; 424/485; 514/944; 514/772.6; 514/774; 514/782; 514/801; 252/315.01; 252/315.3; 252/315.4
[58] Field of Search .................... 424/484, 485, 424/487; 514/944, 772.6, 714, 782, 801; 252/315.01, 315.3, 315.4

[56] References Cited

U.S. PATENT DOCUMENTS 5,135,755  8/1992  Czech et al. .............. 424/487

*Primary Examiner*—Edward J. Webman
*Attorney, Agent, or Firm*—Jennifer K. Farrar; Janal M. Kalis

[57] ABSTRACT

Thermally stable collagen gels formed by the addition of small amounts of neutralized slightly cross-linked polyacrylic acid. Thermally stable gels resulting from 0.3 to 4.0 percent by weight of collagen and 0.10 to 0.50 percent by weight of neutralized slightly cross-linked polyacrylic acid. The thermally stable gels are useful in wound care management. Further, synergistic effects are noted by the addition of 0.5 to 3.0 percent by weight of natural gums, particularly those containing glucuronic acid segments. Gelatin, a partially hydrolyzed collagen, behaves in a similar manner to collagen.

10 Claims, No Drawings

HEAT STABLE WOUND CARE GEL

BACKGROUND OF THE INVENTION

This is a continuation-in-part of Ser. No. 08/145,039 filed Oct. 29, 1993 abandoned which is a continuation of Ser. No. 07/992,264, filed Dec. 14, 1992 abandoned.

This invention relates generally to wound care management and wound care products and, in particular, relates to wound care products based upon thermally stable gels of collagen or partially hydrolyzed collagen.

The present invention also concerns the preparation of thermally stable collagen or partially hydrolysed collagen gels and the use of such gels in wound care management.

By "wound" herein is meant a wide variety of skin sores and most particularly bed sores, pressure sores or sores encountered in the sacrocoxic area of incontinent nursing home patients.

Wound healing occurs by a mechanism in which formation of epidermal tissue and/or collagen eventually cover a wound. In situations where reepithelialization can occur, new epidermis (skin) will cover the wound. In other situations, where wounds with relatively large surface areas must heal, reepithelialization may not be possible and new collagen formation results in a scar tissue covering over the wound.

The use of hydrocolloids in wound care management has been previously described by P. H. Corkhill et al in Biomaterials 10 3–10 (1989). Hydrocolloids absorb aqueous exudate issuing from a wound and in so doing aid in keeping the wound moist. Keeping the wound moist generally hastens the rate of healing and tends to decrease pain. Examples of the types of hydrocolloids believed useful for this purpose include starches, hydrolyzed cellulosics, gums, dry gelatin powder, synthetic polyacrylates and polyacrylamides as well as other water soluble polymers. These hydrocolloid products usually must be used shortly after preparation as they are unstable, particularly when exposed to heat. The requirement for fresh preparation of a hydrocolloid for most treatments drastically increases the labor cost of wound care treatment involving hydrocolloid gels. It is known to employ dry granules of powdered gelatin mixed together with powdered sodium carboxymethyl cellulose and powdered pectin, (available as DuoDerm granules from Convatec, a division of Squibb Co.) and to put such granules into a wound in order to absorb exudate.

It is also known to disperse hydrocolloids in adhesives which are then laminated with an occlusive or non-occlusive covering film to protect, cover and keep a wound moist. Such wound dressings have been described by S. V. Pollack in J. Derm. Surg. Oncology 11(3), 296–300 (1985).

One might speculate that the presence of the collagen in a wound treatment product might aid in new collagen formation thereby further promote wound repair. However, an underlying problem of collagen gels which discourages research and which also discourages any potential widespread commercial use of collagen gels is the general lack of collagen gel thermal stability. For example, a thick collagen gel loses its useful viscosity after heating to about 50° C. (120° F.). Viscosity is necessary for ease of application to the wound, continued adherence to the wound after application and for exudate absorption. By way of example, a wound dressing product marketed by Carrington is a gelled aloe hydrocolloid product for the dressing and management of minor burns, cuts, abrasions, pressure ulcers, stasis ulcers, irritations of the skin and skin conditions associated with periostomy care.

The present invention provides a much needed advance in the field of collagen-based hydrocolloid gel wound care products by providing thermal stability and also is less subject to darkening.

SUMMARY OF THE INVENTION

In light of the above-mentioned thermal instability problem, typical collagen gels have not been widely used for wound care treatment. The inventor has recognized that a solution to the instability problem would open the door to wider distribution and use of a collagen based wound care product. Such a product would retain its usefulness as a wound care treatment product, even though the product might be exposed, possibly only inadvertently, to heat of about 50° C. (120° F.) for as long as two weeks.

The thermal stability of collagen gels has been unexpectedly found to be improved by the addition of small amounts of neutralized slightly cross-linked polyacrylic acid. Thermally stable gels result from compositions with 0.3 to 4.0 percent by weight of collagen and 0.10 to 0.50 percent by weight of neutralized slightly cross-linked polyacrylic acid. Suitable slightly cross-linked polyacrylic acid is available as Carbomer 940 or alternatively Carbomer 980 from B.F. Goodrich. (Carbomer 940 and Carbomer 980 are trade names of B.F. Goodrich for slightly cross-linked polyacrylic acid. These materials have from about 1% to 2% cross-linking resulting from the cross-linking agents allylsucrose or allylpentaerythritol, molecular weight ranges from about 2,000,000 to about 1,000,000,000 daltons and average molecular weights of about 4,000,000 daltons.) By "slightly crosslinked" herein is meant from about 1.0% to about 2.0% cross-linked. Optionally, natural gums, up to as much as 3.0 percent by weight, may be added to the gels of this invention. Synergistic effects are noted by the addition of natural gums, particularly those containing glucuronic acid segments. Gelatin, a partially hydrolyzed collagen, behaves in a similar manner to collagen in this invention.

In a preferred embodiment, the present invention is a thermally stable viscous gel useful as a wound care product. One such gel is prepared from neutralized slightly cross-linked polyacrylic acid, xanthan gum, and collagen. Preferably, the viscosity of a gel of this invention is at least 250,000 cps and most preferably at least 400,000 cps and further the gel of the present invention resists any dramatic decrease in viscosity when exposed to 50° C. (120° F.) for a time period of 2 weeks.

In another preferred embodiment, the present invention is a thermally stable gel of more modest viscosity which is also useful as a wound care product. One such gel is prepared from neutralized slightly cross-linked polyacrylic acid, and collagen. Preferably, the viscosity of a gel of this invention is at least 250,000 cps and further the gel of this embodiment resists any dramatic decrease in viscosity when exposed to 50° C. (120° F.) for a time period of 2 weeks.

Additionally, the present invention includes a process for preparing a thermal stable gel including collagen, wherein the process includes the steps of: providing an aqueous solution of slightly cross-linked polyacrylic acid; optionally adding xanthan gum to the aqueous solution of slightly cross-linked polyacrylic acid solution to form an aqueous slightly cross-linked polyacrylic acid—(optional) xanthan gum mixture; and adding collagen to the aqueous slightly cross-linked polyacrylic acid mixture—(optional) xanthan gum mixture. Preferably, the aqueous solutions are heated to 50° C. (120° F.) for the preparation process.

Further, the present invention includes a method of treating a wound, wherein the method includes: providing a thermally stable collagen gel, and applying the gel to a surface wound.

In a preferred embodiment, a thermally stable gel includes

| | |
|---|---|
| 90–98% | water |
| 1–3% | collagen |
| 0.01–2% | panthenol |
| 0.01–2% | xanthan gum |
| 0.01–1.5% | allantoin |
| 0.01–1.25% | Carbomer 940 (or Carbomer 980) |
| 0.01–1.2% | triethanolamine |
| 0.01–0.40% | methyl paraben |
| 0.01–0.20% | diazolidinyl urea |
| 0.01–0.20% | tetrasodium EDTA |
| 0.01–0.18% | citric acid |

In a most preferred embodiment, the thermal stable gel includes

| | |
|---|---|
| 94.22% | water |
| 2.00% | collagen |
| 1.00% | panthenol |
| 1.00% | xanthan gum |
| 0.60% | allantoin |
| 0.35% | Carbomer 940 (or Carbomer 980) |
| 0.39% | triethanolamine |
| 0.16% | methyl paraben |
| 0.16% | diazolidinyl urea |
| 0.07% | tetrasodium EDTA |
| 0.05% | citric acid |

Additionally, the present invention includes a process for preparing a less viscous thermally stable gel including collagen, wherein the process includes the steps of: providing an aqueous solution of slightly cross-linked polyacrylic acid; and adding collagen to the polyacrylic acid. Preferably, the aqueous polyacrylic acid solutions are heated to 50° C. (120° F.) for the preparation process. The gel is characterized by viscosity of from about 450,000 to 500,000 cps when initially formed. The viscosity rises over a period of about two weeks to about 600,000 cps.

In another most preferred embodiment, characterized by lower viscosity for easier application to patients, a lower viscosity thermally stable gel includes:

| | |
|---|---|
| 96.27% | water |
| 0.50% | collagen |
| 1.00% | panthenol |
| 0.60% | allantoin |
| 0.50% | slightly cross-linked polyacrylic acid (Carbomer 940) |
| 0.63% | triethanolamine |
| 0.20% | methyl paraben |
| 0.20% | diazolidinyl urea |
| 0.07% | tetrasodium EDTA |
| 0.03% | citric acid |

In order to eliminate traces of benzene present in the Carbomer 940, yet another most preferred embodiment with thermally stable lower viscosity, is prepared employing the benzene-free slightly cross-linked (i.e. about 1–2% cross-linked) polyacrylic acid Carbomer 980 instead of Carbomer 940 as follows:

| | |
|---|---|
| 96.20% | water |
| 0.55% | slightly cross-linked polyacrylic acid (Carbomer 980) |
| 0.65% | triethanolamine |
| 1.00% | panthenol |
| 0.60% | allantoin |
| 0.03% | citric acid |
| 0.07% | tetrasodium EDTA |
| 0.20% | methyl paraben |
| 0.20% | diazolidinyl urea |
| 0.50% | collagen |

It has also been observed that addition of the ingredients in the order listed provides a slightly more viscous gel and better clarity than when a gel is prepared by altering the order of addition.

Yet another most preferred embodiment with thermally stable lower viscosity and a variation in the preservative system is prepared with Carbomer 980 as follows:

| | |
|---|---|
| 96.20% | water |
| 0.55% | slightly cross-linked polyacrylic acid (Carbomer 980) |
| 0.65% | triethanolamine |
| 1.00% | panthenol |
| 0.60% | allantoin |
| 0.03% | citric acid |
| 0.07% | tetrasodium EDTA |
| 0.15% | methyl paraben |
| 0.05% | propyl paraben |
| 0.20% | diazolidinyl urea |
| 0.50% | collagen |

Again, it has also been observed that addition of the ingredients in the order listed provides a slightly more viscous gel and better clarity than a gel prepared by altering the order of addition. The inclusion of both methyl paraben and propyl paraben in a ratio of about 3 to 1 is believed to provide a microbial preservative system capable of consistent manufacture below 10 colony forming units.

DETAILED DESCRIPTION OF THE PREFERRED EMBODIMENTS

Collagen gel is a natural hydrocolloid capable of absorbing large quantities of moisture. Collagen is the primary structural protein of multicelled organisms and has as its basic structure a triple stranded cross-linked helix. The individual collagen molecule or tropocollagen is a rod-shaped triple helix having a molecular weight of approximately 375,000 daltons. In contrast, the collagen source preferably employed in preparation of the gels of the present invention is a single strand from such a triple helix and has a molecular weight of about 115,000 daltons. The source of the collagen is collagen strands with a molecular weight of about 100,000 to 120,000 daltons derived from animal tropocollagen cross-linked triple-helix. Gelatin, a partially hydrolyzed collagen, having an average molecular weight of 110,000 daltons, has also been used successfully in preparing the thermally stable gels of this invention.

A collagen or gelatin gel may be prepared from single strand collagen by dissolving the protein in water at about 50° C. (120° F.) and then cooling back to room temperature while mixing and stirring. At room temperature (77° F.), these gels are stable over long periods of time. However, if such gels are again heated to 50° C. (120° F.) and held at such an elevated temperature for a few days, upon recooling to room temperature, the gel structure does not reform and the system has a water-like viscosity. Since temperatures of this nature are often encountered in non-refrigerated truck interiors or standing in non-air conditioned warehouse interiors on hot days, it is quite probable that shipments of collagen gel product exposed to such temperatures could lose their useful viscous gel-structure and be converted to a thin water-like viscosity. In other words, initially, upon recooling to room temperature, the viscosity of the reheated gel is only about 4 centipoise. After standing for 6 weeks at room temperature, the viscosity has a minor recovery of viscosity to about 25,000 centipoise and does not increase significantly thereafter. Since it is the gel viscosity that allows for convenient application of the product to a wound, for example, from a squeeze tube and subsequent retention on the wound and it is the gel structure which absorbs wound exudate, loss of gel structure results in a dramatic loss of this desirable wound management attribute. This lack of thermal stability severely limits the commercial use of collagen (or gelatin) gels as wound management products.

The inventor's research has demonstrated that the use of antioxidants such as ascorbic acid or butylated hydroxytoluene (BHT) does not prevent gel degradation upon heating to 50° C. Also, the addition of common chelating agents such as ethylenediamine tetra-acetic acid or its salts or citric acid also does not prevent gel degradation at 50° C., but it does prevent color formation. The viscosity instability after a few days storage at 50° C. (120° F.) after gel formation is shown in Table I. However, it has been discovered that addition of a neutralized slightly cross-linked polyacrylic acid, such as Carbomer 940, can provide thermal stability in a hydrocolloid gel based primarily upon collagen (or gelatin.) Preferably, the ratio of polyacrylic acid to collagen is from about 1:1 to about 1:6. Carbomer 980 can also serve as a slightly cross-linked polyacrylic acid effectively in this regard.

A preferred embodiment of the invention includes about 94.22% water and about 2.00% collagen; along with about 1.00% panthenol (which is believed to aid wound moisturization); 1.00% xanthan gum (a suspension and viscosity agent); about 0.35% Carbomer 940 (which is believed to provide the thermal stability in the final gel); about 0.39% triethanolamine (which is believed to reinforce the function of the Carbomer 940 by neutralization); about 0.07% tetrasodium EDTA, (which is believed to prevent discoloration); 0.60% allantoin (which is believed to function as an anti-irritant); 0.16% of methyl paraben and 0.16% of diazolidinyl urea (preservatives) and 0.05% of citric acid (a pH buffer). The above-stated functions of the invention components are the inventor's good faith belief and are not intended to limit the invention.

A most preferred embodiment of the invention includes about 96.27% water and about 0.50% collagen; along with about 1.00% panthenol (which is believed to aid wound moisturization); about 0.50% Carbomer 940 (which is believed to provide the thermal stability in the final gel); about 0.63% triethanolamine (which is believed to reinforce the function of the Carbomer 940 by neutralization); about 0.07% tetrasodium EDTA, (which is believed to prevent discoloration); 0.60% allantoin (which is believed to function as an anti-irritant); 0.20% of methyl paraben and 0.20% of diazolidinyl urea (preservatives) and 0.03% of citric acid (a pH buffer). The above-stated functions of the invention components are the inventor's good faith belief and are not intended to limit the invention.

The invention is further illustrated by the examples that follow. In these examples, all parts are parts by weight based on a total of 100 parts.

EXAMPLE 1

(Comparative Example)

To 97.68 parts of water at 50° C. (120° F.) was added 2.00 parts of collagen. After mixing under rapid propeller agitation until the collagen was dissolved, 0.16 parts of methyl paraben and 0.16 parts of Germall II (Trade name of Sutton Labs Inc. for diazolidinyl urea) were added as preservatives and dissolved. After dissolution of all ingredients was achieved, the solution was cooled to room temperature and allowed to sit overnight for gelation to occur. Samples of this gel were allowed to age at room temperature while others were heated at 50° C. (120° F.) for four days and then cooled to room temperature. Table I shows test data from Example 1.

EXAMPLE 2

(Comparative Example)

To 97.68 parts of water at 50° C. (120° F.) was added 2.00 parts of gelatin (275 Bloom) which was rapidly stirred until the gelatin was dissolved. Then 0.16 parts of methyl paraben and 0.16 parts of Germall II were added as preservatives and dissolved. After complete dissolution of the solids was achieved, the solutions were cooled to room temperature and let stand overnight whereupon gelation occurred. Samples of this gel were allowed to age at room temperature while others were heated at 50° C. (120° F.) for four days and then cooled to room temperature. Table I shows test data from Example 2.

EXAMPLE 3

A gel having the formulation of 98.94% water, 0.35% Carbomer 940, 0.16% each of methyl paraben and Germall II and 0.39% triethanolamine (TEA) was prepared by first dissolving the Carbomer 940 in water at 50° C. under rapid agitation. The methyl paraben and diazolidinyl urea were then dissolved after which the triethanolamine was added to neutralize the system and thicken it. Samples of this gel were allowed to age at room temperature while others were heated at 50° C. (120° F.) for two weeks. Test results are shown in Table I.

EXAMPLE 4

To demonstrate the effect of the Carbomer 940 on collagen, the system shown in Example 4 was prepared. A gel consisting of 96.94% water, 0.35% Carbomer 940, 0.16% each of methyl paraben and diazolidinyl urea, 2.0% collagen, and 0.39% TEA, was prepared as follows. Water at about 50° C. (120° F.) was added to a beaker and the Carbomer 940 added under very rapid propeller agitation. The methyl paraben and diazolidinyl urea was then added followed by neutralization with triethanolamine, after which 2.0% collagen was dissolved in the system. Viscosities of Example 4 as a function of time and temperature are shown in Table I. Note that Example 4 lacks the optional natural gum, xanthan gum. It was observed that there is hysteresis in such a system upon shear.

EXAMPLE 5

The use of xanthan gum in thickening, improving and obtaining uniform flow properties of viscous systems is well known. Therefore, a 1.0% solution of xanthan gum was prepared in water (along with a small amount of the preservatives.) The viscosity of this solution should approximately indicate the xanthan gum contribution to the total viscosity if there were no strong interactions of the xanthan gum with other ingredients. Samples were treated as outlined in below and test results are shown in Table I. Specifically, to 98.68 parts of water at 50° C. (120° F.) was added 1.00 part of xanthan gum under rapid agitation. A hazy suspension or solution was obtained to which was then added 0.16 parts each of methyl paraben and diazolidinyl urea. Samples were tested as detailed in Examples 3 and 4 and the viscosity of this system as a function of temperature and time is shown in Table I.

EXAMPLE 6

To 95.94 parts of water at 125° F. was added 0.35 parts of Carbomer 940 under very rapid agitation. Upon dissolution of the Carbomer 940, the Carbomer 940 solution was neutralized with 0.39% triethanolamine. Then 1.0% xanthan gum was added to the system and agitated until dissolution was achieved. 0.16 parts each of methyl paraben and diazolidinyl urea were dissolved in the system. The last item to be dissolved in the preparation of Example 6 was 2.0% of collagen. Here again, the samples from Example 6 were tested as above and the viscosity data as a function of time and temperature is shown in Table I. It should also be noted that there was very little hysteresis as a function of shear in the samples from Example 6.

EXAMPLE 7

(Comparative Example)

Example 7 was a gel prepared by dissolving 0.35% of Carbomer 940 in 96.22% water at 50° C. (120° F.) under rapid propeller agitation. After the Carbomer 940 was completely dissolved, 1.00% of xanthan gum was dissolved and the Carbomer 940 was then neutralized with 0.39% TEA. Next, 1.00% panthenol, 0.60% allantoin, 0.16% methyl paraben, 0.16% diazolidinyl urea, 0.05% citric acid and 0.07% tetrasodium EDTA are dissolved in the system. The viscosity on standing at room temperature (RT) and after heating at 50° C. (120° F.) are shown in Table I.

EXAMPLE 8

Example 8 was a gel prepared by dissolving 0.35% of Carbomer 940 and 2.00% collagen in 94.22% water at 50° C. (120° F.) under rapid propeller agitation. After the Carbomer 940 and collagen was completely dissolved, 1.00% of xanthan gum was dissolved and the Carbomer 940 was then neutralized with 0.39% TEA. Then 1.00% panthenol, 0.60% allantoin, 0.16% methyl paraben, 0.16% diazolidinyl urea, 0.05 citric acid and 0.07% tetrasodium EDTA were dissolved in the system. The viscosity after standing at room temperature and after heating at 50° C. (120° F.) are shown in Table I.

EXAMPLE 9

Example 9 was a gel prepared by dissolving 0.35% of Carbomer 940 in 97.94% water at 50° C. (120° F.) under rapid agitation to avoid gel formation of the Carbomer 940. After the Carbomer 940 was completely dissolved it was neutralized with 0.39% triethanolamine. Then 1.00% xanthan gum, 0.16% methyl paraben and 0.16% diazolidinyl urea were added and dissolved. The viscosity values of this system at room temperature and after heating are shown in Table I.

TABLE I

Effect of Time and Temperature on Viscosity Stability of Examples 1 & 2 and 3–8

| Example | Viscosity (Cps) @ RT 1 Day After Mfg | Viscosity (cps) @ RT After Heating @ 120° F. For 2 Weeks & Cooling Back to RT | Viscosity @ RT After 6 Weeks Standing @ RT |
|---|---|---|---|
| 1 | >3.16 × 10$^6$ | 5.0* | 3.16 × 10$^6$ |
| 2 | >3.16 × 10$^6$ | 4.0* | 3.16 × 10$^6$ |
| 3 | 275,000 | 220,000 | 280,000 |
| 4 | 920,000 | 351,000 | 900,000 |
| 5 | 23,000 | 28,000 | 24,000 |
| 6 | 983,000 | 420,000 | 3.12 × 10$^6$ |
| 7 | 218,000 | 234,000 | 216,000 |
| 8 | 702,000 | 460,000 | 790,000 |
| 9 | 359,000 | 289,000 | 351,000 |

*heated for only 4 days rather than 2 weeks (RT means room temperature (77° F.))

As can be seen from Example 3 in Table I, the viscosity stability of a gel including Carbomer 940 to which a little preservative has been added shows little effect due to exposure to elevated temperature and/or storage over an extended time period. The percentage of Carbomer and triethanolamine used results in a thermally stable gel of about 250,000 cps.

Example 4 indicates the effect of the Carbomer 940 neutralized gel on collagen. It should be noted that a gel of over 3,000,000 cps is not produced by the collagen in the presence of TEA neutralized Carbomer 940 upon preparation at 50° C.) (120° F.) and cooling to room temperature overnight. It is theorized that amino groups on the collagen are hydrogen-bonding to acrylic acid moieties of the Carbomer 940 rather than amino acid groups on other collagen chains preventing cross-linked collagen molecules from forming. This inhibiting of the degree of cross-linking shown by collagen itself in Example 1 of Table I can be seen by the differences in viscosity at room temperature. It should also be noted in Table I, that after heating for two weeks at 50° C. (120° F.), Example 4 does not fall to the base level of the Carbomer 940 gel alone after heating (demonstrated by Example 3 as shown in Table I), this indicates that some cross-linked collagen structure was not destroyed upon heating at 50° C. (120° F.) for two weeks. Upon standing at room temperature alone for several weeks, the viscosity of Example 4 appears thermally stable.

Example 5 illustrates the viscosity of a 1.0% xanthan gum solution in water in the presence of the standard preservatives used. As can be seen in Table I, the viscosity of the 1.0% xanthan gum solution is not effected by either elevated temperature 50° C. (120° F.) or time.

Example 6 illustrates the viscosity stability of 2.0% collagen in the presence of a Carbomer gel and xanthan gum. As can be seen in Table I, when the gel system is produced as described in Example 6, the expected initial viscosity is obtained. This viscosity is approximately the sum of the initial viscosities of Examples 4 and 5. However, on standing for several weeks at room temperature, a viscosity equal to that of the collagen gel alone (see Example 1) is observed. It is theorized that the glucuronic moieties of xanthan gum loosely interact with the amino groups of the collagen thus interfering with the interaction of collagen and polyacrylic acid which is shown in Example 4 and Table I. With time, the amine groups can cross-link with collagen amino acid moieties. Again it should also be noted that the viscosity after two weeks at 50° C. (120° F.) does not revert to a water-like consistency. The viscosity is significantly larger from that expected from the sum of viscosities which might be expected from addition of 1.0% xanthan gum to a collagen-Carbomer 940 gel (as illustrated in the test results of Examples 4 and 5 of Table I.) This may indicate that the presence of the optional natural gum (xanthan gum) in Carbomer 940 stabilized collagen gel may help to stabilize the cross-linking of the amino groups of the collagen chains. Such interaction might also contribute to the very high (over 3,000,000 cps) viscosity observed at room temperature several weeks after manufacture. Thus, a synergistic effect of natural gum has been discovered in addition to the basic discovery of thermally stabilizing collagen gels with neutralized slightly cross-linked polyacrylic acid.

Other ingredients which might be helpful in a wound dressing, such as panthenol, allantoin, tetrasodium EDTA, and the like tend to lower the overall viscosity of the collagen gel.

In comparing the results of Examples 6 and 8, it can be seen that the addition of panthenol, allantoin, tetrasodium EDTA and citric acid (Example 8) lowers the viscosity of the gel at room temperature. However, the gel which results on overnight cooling to room temperature after being heated at 120° F. for two weeks is a little more viscous. This is probably due to the increased thermal stability due to the tetrasodium EDTA and citric acid. At the same time, the panthenol, allantoin, tetrasodium EDTA and citric acid interfere with hydrogen-bonding between collagen molecules.

Similar phenomena are observed in comparison of the results from Examples 7 and 9. The addition of panthenol, allantoin, tetrasodium EDTA and citric acid reduces the viscosity of the Carbomer 940 with (optional) xanthan gum gel in Example 7 compared to that of Example 9. Since thermal stability of collagen molecules is not involved in Examples 7 and 9, the viscosity decrease due to the additives in Example 9 is also evident after 2 weeks heating at 120° F. as shown in Table I.

In a gel matrix including neutralized polyacrylic acid, triethanolamine and xanthan gum, the collagen gel still exhibits better structural aspects after accelerated aging (two weeks at 50° C. (120° F.)) than the complete gel breakdown exhibited by the collagen itself (Example 1, Table I). This is illustrated in Example 8.

Example 8 which has the same ingredients as Example 7 plus 2.00% collagen has a viscosity of 702,000 cps after standing at room temperature for 24 hours. This increases to 790,00 cps several weeks later. Upon heating to 50° C. (120° F.) for two weeks, the viscosity falls to 460,000 cps. Since the base gel without collagen has a viscosity of about 220,000 cps, it indicates that the collagen still has a gel-like structure and therefore is thermally stable relative to that of Example 1.

In summary, the results presented in Table I demonstrate that the collagen and gelatin gels prepared by the formulations of this invention are substantially thermally stable relative to mere collagen gels with or without minor amounts of preservatives present.

Samples from Examples 10 and 11 were tested as outlined in Examples 3 and 4.

EXAMPLE 10

Example 10 illustrates the effect of a Carbomer containing gel whose formulation is 0.25% Carbomer 940, 1.00% xanthan gum, 0.29% triethanolamine, 0.16% methyl paraben, 0.16% Germall II (diazolidinyl urea) and 98.14% water at 50° C. (120° F.). The Carbomer 940 is dissolved after which the polyacrylic acid was neutralized with 0.29% TEA and then the 0.16% each of methyl paraben and Germall II were dissolved.

EXAMPLE 11

Example 11 is a formulation of 96.14% water at 50° C. (120° F.), 0.25% Carbomer 940, 1.0% xanthan gum, 0.29% TEA, 2.00% gelatin (275 Bloom) and 0.16% each of methyl paraben and Germall II. This formulation was prepared in the same manner as Example 9 with the gelatin being dissolved last.

The viscosity data of Examples 10 and 11 are shown in Table II. As seen in Table II, the viscosity of Example 11, i.e. 335,000 cps after two weeks of heating at 50° C. (120° F.), indicates gel structure contributed by the gelatin (275 Bloom) as the viscosity of the comparative gel system (i.e. without the gelatin) is only 85,000 cps. Referring back to Example 2 of Table I, the viscosity of gelatin without the polyacrylic acid is only 4 cps. Hence, gel structure of the gelatin, in the presence of neutralized, slightly cross-linked acrylic acid, is maintained after heating, presumably in a similar manner observed in collagen in the presence of neutralized slightly cross-linked acrylic acid (Example 6 in Table II).

TABLE II

| | Effect of Time and Temperature on Gelatin Gels | | |
| --- | --- | --- | --- |
| Example | Viscosity (cps) @ RT One Day After MFG | Viscosity (cps) @ RT After heating @ 120° F. for 2 Weeks | Viscosity @ RT After 6 Weeks Standing @ RT |
| 10 | 84,000 | 86,000 | 83,000 |
| 11 | 624,000 | 335,000 | $3.12 \times 10^6$ |

Notes:
RT means room temperature.
MFG means date of preparation.

EXAMPLE 12

Example 12 was a formulation wherein the Carbomer 940 was neutralized with 2-aminomethylpropanol (2-AMP) instead of triethanolamine (TEA) and consisted of 97.94 parts of water at 50° C. (120° F.), 0.35 parts Carbomer 940, 0.39 parts 2-AMP, 1.0 part xanthan gum, 0.16 parts methyl paraben and 0.16 parts Germall II. Neither collagen nor gelatin were present in Example 12.

EXAMPLE 13

Example 13 was a formulation similar to Example 12 but contained 2.0 parts collagen and consisted of 95.94% water at 50° C. (120° F.), 0.35% Carbomer 940, 0.39% 2-AMP, 1.0% xanthan gum, 0.16% methyl paraben, 0.16% Germall II and 2.0% collagen.

Samples from Examples 12 and 13 were tested as detailed in Example 3 above. The viscosity, time, temperature data from the testing of Examples 12 and 13 are shown in Table III.

TABLE III

Time and Temperature Effect on Viscosity of
Triethanolamine Containing Examples 12 and 13
(Example 6 Results Repeated for Comparison)

| Example | Viscosity at RT 1 Day after MFG | Viscosity at RT After Heating @ 120° F. for 2 wks | Viscosity after 6 Wks at RT |
| --- | --- | --- | --- |
| 6 | 983,000 | 420,000 | $3.12 \times 10^6$ |
| 12 | 94,000 | 82,000 | 97,000 |
| 13 | 222,000 | 210,000 | 226,000 |

The higher degree of neutralization of the polyacrylic acid moieties by TEA compared to an equal weight percent of 2-AMP results in the higher viscosity of Example 9 (Table I) compared to that of Example 12.

EXAMPLE 14

A thermally stable gel with modest viscosity was formed from 94.22% water at about 50° C. by first dissolving 0.50% of slightly cross-linked polyacrylic acid (Carbomer 940), adding 0.63% triethanolamine, 0.60% allantoin, 1.00% panthenol, 0.20% methyl paraben, 0.20% diazolidinyl urea, 0.07% tetrasodium EDTA, and 0.03% citric acid. Next 0.50% collagen was added. The gel of Example 14 had a viscosity of roughly about 600,000 centipoise after being held for one day at room temperature, about roughly about 500,000 centipoise upon cooling after a two week exposure to 50° C. and very little change in viscosity when subjected to subsequent heat cycles.

EXAMPLE 15

A slightly less viscous gel was prepared from the following ingredients:

| | |
| --- | --- |
| 96.35% | water (at about 50° C.) |
| 0.50% | slightly cross-linked polyacrylic acid (Carbomer 940) |
| 0.63% | triethanolamine |
| 1.00% | panthenol |
| 0.60% | allantoin |
| 0.03% | citric acid |
| 0.07% | tetrasodium EDTA |
| 0.16% | methyl paraben |
| 0.16% | diazolidinyl urea (Germall II) |
| 0.50% | collagen |

Viscosity of the gel after preparation was 468,000 cps and pH was 6.80. After heating for two weeks at 50° C. (120° F.) followed by cooling to room temperature overnight, the viscosity was 491,000 cps.

EXAMPLE 16

Another slightly less viscous gel was prepared from the following ingredients:

| | |
| --- | --- |
| 96.29% | water (at about 50° C.) |
| 0.55% | slightly cross-linked polyacrylic acid (Carbomer 980) |
| 0.64% | triethanolamine |
| 1.00% | panthenol |
| 0.60% | allantoin |
| 0.03% | citric acid |
| 0.07% | tetrasodium EDTA |
| 0.16% | methyl paraben |
| 0.16% | diazolidinyl urea (Germall II) |
| 0.50% | collagen |

The viscosity and pH properties of the gel of example 16 were similar to those of example 15. Because this gel includes Carbomer 980 rather than Carbomer 940 as a source of slightly cross-linked polyacrylic acid, it is free of any benzene residue.

EXAMPLE 17

An even less viscous gel was prepared from the following ingredients:

| | |
| --- | --- |
| 96.74% | water (at about 50° C.) |
| 0.35% | slightly cross-linked polyacrylic acid (Carbomer 940) |
| 0.39% | triethanolamine |
| 1.00% | panthenol |
| 0.60% | allantoin |
| 0.03% | citric acid |
| 0.07% | tetrasodium EDTA |
| 0.16% | methyl paraben |
| 0.16% | diazolidinyl urea (Germall II) |
| 0.50% | collagen |

Viscosity of the gel of example 17 after preparation was 159,000 cps and pH was 6.82. After heating for two weeks at 50° C. (120° F.) followed by cooling to room temperature overnight, the viscosity was 154,000 cps.

In summary, the loss viscosity after heating and typical minor viscosity recovery is avoided by including neutralized slightly cross-linked polyacrylic acid in a collagen gel. The thermally stable gels of this invention may be used as wound care products by applying directly to affected areas of skin and are believed to be better in efficacy and action than products such as Carrington Wound Care Gel due to the larger amounts of hydrocolloids in the gels of the present invention. The preferred gels of this invention are also characterized by good thermal stability with respect to viscosity and color. The color of the thermally stable gels of this invention does not darken substantially during aging or temperature simulated accelerated aging when tetrasodium EDTA has been included.

Although the present invention has been described with reference to the preferred embodiments, workers skilled in the art will recognize that changes may be made in form and detail without departing from the spirit and scope of the invention.

The terms and expressions which have been employed are used as terms of description and not of limitation, and there is no intention in the use of such terms and expressions of excluding any of the features shown and described or portions thereof, but it is recognized that various modifications are possible within the scope of the invention claimed.

What is claimed is:

1. A hydrocolloid wound care gel made from substances comprising:

slightly cross-linked polyacrylic acid gel in a concentration of about 0.3 to 0.7% by weight;

a neutralizing substance for neutralizing the slightly cross-linked polyacrylic acid gel in a concentration of about 0.3 to 0.7% by weight selected from the group consisting of triethanolamine and 2-aminomethylpropanol;

collagen in a concentration of about 0.05 to 4% by weight or gelatin in a concentration of about 0.1 to 0.5% by weight; and water in a concentration range of about 94 to 96% by weight, and has a minimum viscosity of about 150,000 cp when the gel is heated to 50 degrees C. and held at 50 degrees C. for two weeks and then cooled to room temperature.

2. The thermally stable hydrocolloid wound care gel of claim 1 and wherein the viscosity is at least 250,000 cps after reheating to 50° C. (120° F.) for 2 weeks followed by cooling to room temperature.

3. The gel of claim 1 and wherein the extent of cross-linking in the slightly cross-linked polyacrylic acid is from about 1% to about 2%.

4. The gel of claim 1 and wherein the slightly cross-linked polyacrylic acid is neutralized with triethanolamine.

5. A wound care product comprising:

| | |
|---|---|
| 94.22% | water |
| 2.00% | collagen |
| 1.00% | panthenol |
| 1.00% | xanthan gum |
| 0.60% | allantoin |
| 0.35% | slightly cross-linked polyacrylic acid |
| 0.39% | triethanolamine |
| 0.16% | methylparaben |
| 0.16% | diazolidinyl Urea |
| 0.07% | tetrasodium EDTA |
| 0.05% | citric Acid |

6. A wound care product comprising:

| | |
|---|---|
| 96.20% | water |
| 0.55% | slightly cross-linked polyacrylic acid (Carbomer 980) |
| 0.65% | triethanolamine |
| 1.00% | panthenol |
| 0.60% | allantoin |
| 0.03% | citric acid |
| 0.07% | tetrasodium EDTA |
| 0.15% | methyl paraben |
| 0.05% | propyl paraben |
| 0.20% | diazolidinyl urea |
| 0.50% | collagen |

7. A process for preparing a wound care gel comprising the steps of:

providing an aqueous solution of slightly cross-linked polyacrylic acid in a concentration of about 0.3 to 0.7% by weight;

neutralizing the aqueous solution with a neutralizing material selected from the group consisting of triethanolamine and 2-aminomethylpropanol;

heating water to a temperature of about 50° C. and adding collagen to the heated water; and adding the collagen in a concentration range of about 0.5 to 4% by weight to the neutralized aqueous solution, and when the gel is heated to 50 degrees C. for two weeks and then cooled to room temperature, the gel has a minimum viscosity of about 150,000 cp.

8. The process of claim 7 and further comprising the step of:

adding xanthan gum to the neutralized aqueous solution of polyacrylic acid.

9. The process of claim 7 and further comprising the step of:

adding preservatives and anti-irritants.

10. A method of treating a wound, comprising the step of:

applying to the wound a gel comprising: slightly cross-linked polyacrylic acid in a concentration range of about 0.3 to 0.7% by weight and collagen in a concentration of about 0.05 to 4% by weight; and water in a concentration range of about 94 to 97% by weight, the gel having a minimum viscosity of about 150,000 cp when the gel is heated to 50 degrees C. and held at 50 degrees C. for two weeks and then cooled to room temperature.

\* \* \* \* \*